United States Patent
Björnberg et al.

(10) Patent No.: US 8,748,689 B2
(45) Date of Patent: Jun. 10, 2014

(54) DEVICE FOR THE TREATMENT OF VAGINAL FUNGAL INFECTION

(75) Inventors: Sten Björnberg, Spånga (SE); Jan G. Smith, Askim (SE)

(73) Assignee: Abigo Medical AB, Askim (SE)

( * ) Notice: Subject to any disclaimer, the term of this patent is extended or adjusted under 35 U.S.C. 154(b) by 830 days.

(21) Appl. No.: 12/290,899

(22) Filed: Nov. 5, 2008

(65) Prior Publication Data

US 2009/0131909 A1  May 21, 2009

Related U.S. Application Data

(60) Provisional application No. 61/001,889, filed on Nov. 5, 2007.

(51) Int. Cl.
*A61F 13/15* (2006.01)

(52) U.S. Cl.
USPC .......................................... 604/359; 604/360

(58) Field of Classification Search
USPC .................................................. 604/359, 360
See application file for complete search history.

(56) References Cited

U.S. PATENT DOCUMENTS

| | | | |
|---|---|---|---|
| 4,211,227 A | 7/1980 | Anderson et al. | |
| 4,275,721 A | 6/1981 | Olson | |
| 4,617,326 A * | 10/1986 | Bjornberg et al. | 428/536 |
| 4,642,108 A | 2/1987 | Sustmann | |
| 4,643,180 A | 2/1987 | Feld et al. | |
| 4,643,181 A | 2/1987 | Brown | |
| 4,655,756 A | 4/1987 | Fawkes | |
| 4,678,704 A | 7/1987 | Fellows | |
| 4,832,009 A | 5/1989 | Dillon | |
| 5,098,417 A | 3/1992 | Yamazaki et al. | |
| 5,380,294 A | 1/1995 | Persson | |
| 5,447,492 A | 9/1995 | Cartmell et al. | |
| 5,464,610 A | 11/1995 | Hayes, Jr. et al. | |
| 5,497,789 A | 3/1996 | Zook | |
| 5,498,416 A | 3/1996 | Carsenti-Etesse et al. | |
| 5,700,742 A | 12/1997 | Payne | |
| 5,707,736 A | 1/1998 | Levy et al. | |
| 5,753,256 A | 5/1998 | Cordes et al. | |
| 5,817,325 A | 10/1998 | Sawan et al. | |
| 5,856,248 A | 1/1999 | Weinberg | |
| 5,941,840 A | 8/1999 | Court et al. | |
| 6,037,431 A | 3/2000 | Shioji et al. | |
| 6,160,196 A | 12/2000 | Knieler et al. | |
| 6,369,289 B1 | 4/2002 | Orr, III | |

(Continued)

FOREIGN PATENT DOCUMENTS

| DE | 100 20 989 A1 | 4/2000 |
|---|---|---|
| EP | 0 475 807 A2 | 3/1992 |

(Continued)

OTHER PUBLICATIONS

Claesson, M. A promising alternative in the treatment of dermal fungal infections, found Jan. 12, 2010 at http://www.cutimed-sorbact.es/PDF/Fungal_infec.pdf.

*Primary Examiner* — Melanie Hand
(74) *Attorney, Agent, or Firm* — Lynn E. Barber

(57) ABSTRACT

An absorbent article, e.g. tampons, sanitary napkins, panty liners and the like, and the process for their preparation in which a hydrophobic and/or cationactive layer is attached to a conventional absorbent layer, for the binding of microorganisms, specifically for treating or alleviating or prophylactically preventing vaginal fungal infections.

21 Claims, 4 Drawing Sheets

(56) References Cited

U.S. PATENT DOCUMENTS

| | | |
|---|---|---|
| 6,416,779 B1 | 7/2002 | D'Augustine et al. |
| 7,576,256 B2 | 8/2009 | Bjornberg et al. |
| 2003/0068331 A1 | 4/2003 | Battaglia et al. |
| 2003/0224034 A1 * | 12/2003 | Koenig .................. 424/443 |
| 2004/0082925 A1 | 4/2004 | Patel |
| 2004/0127831 A1 | 7/2004 | Sigurjonsson |
| 2004/0161452 A1 | 8/2004 | Petit |
| 2004/0265362 A1 | 12/2004 | Susilo |
| 2006/0163149 A1 | 7/2006 | Wadstrom et al. |
| 2006/0165761 A1 | 7/2006 | Trotter |
| 2006/0264857 A1 | 11/2006 | Colbert |
| 2008/0177214 A1 | 7/2008 | Robertsson et al. |
| 2008/0249485 A1 | 10/2008 | Effing |

FOREIGN PATENT DOCUMENTS

| | | |
|---|---|---|
| WO | WO 92/13577 | 8/1992 |
| WO | WO 2004/017881 A1 | 3/2004 |
| WO | WO 2005/067991 A1 | 7/2005 |
| WO | WO 2007/062024 A1 | 5/2007 |
| WO | WO 2007/073246 A1 | 6/2007 |

* cited by examiner

DEVICE FOR THE TREATMENT OF VAGINAL FUNGAL INFECTION

CROSS-REFERENCE TO RELATED APPLICATIONS

This application claims priority from U.S. provisional application Ser. No. 61/001,889 filed Nov. 5, 2007.

BACKGROUND OF THE INVENTION

1. Field of the Invention

The present invention relates generally to absorbent articles, such as catamenial articles, e.g. tampons, sanitary napkins, panty liners etc. and the process for their preparation. More particularly the invention relates to the combination of a hydrophobic and/or cationactive layer attached to a conventional absorbent layer, for the binding of microorganisms, specifically for treating or alleviating or prophylactically preventing fungal vaginal infections especially from *Candida albicans*.

2. Description of the Prior Art

The so-called SORBACT® line of products consists of cellulose acetate fabric, cotton gauze or nonwoven (hereinafter named the SORBACT® material) treated with the fatty acid ester, for example DACC (dialkyl carbamoyl chloride) and/or AKD (alkyl ketene dimer). The treatment with fatty acid esters provides the SORBACT® material with a strong hydrophobic property. Numerous studies during the last few decades have shown that pathogenic microorganisms, such as *Staphylococcus aureus*, Group A streptococci and the yeast *Candida albicans* commonly express profound cell surface hydrophobicity. The microorganisms in the exudates from the wound needing to be treated will accompany the flow of liquid absorbed into the absorbing material and come in contact with the hydrophobic component and bind. Another antimicrobial property of the SORBACT® product is its cation activity, described in US Patent application 2006/0163149. The exterior membranes of mammalian cell exterior membranes are generally neutral. Thus the positively charged SORBACT® material preferentially binds to the negatively charged membranes of microorganisms.

The so called SORBACT®-principle discussed above is a modern and overall effective method for anti-microbial wound healing, which is described in U.S. Pat. No. 4,617,326 and U.S. Patent application 2006/0129080. Products utilizing the SORBACT® principle are commercially available. However none of the prior art describes the SORBACT® principle in combination with sanitary protection articles for protection against fungal vaginal infections.

Fungal infections and growth may occur at many places including the human body, e.g. in the vagina or in the oral cavity. Invasive fungal infections are increasing because of the growing number of immunocompromised patients (Jones, J. M. 1990. Laboratory diagnosis of invasive candidiasis. Clin Microbiol Rev 3:32-45). Many of these infections occur in critically ill patients suffering from an underlying disease. Over the past decades "*Candida* overgrowth" has increasingly been a problem as a result of several factors including the abundant use of antibiotics in medicine.

*Candida* vaginitis is an infection of the vagina. It causes a foul smelling, sticky, white-yellow discharge that may be accompanied by itching, burning and swelling. Such an infection can also make walking, urinating, or intercourse painful. Generally, the vaginal cavity exhibits an aqueous environment containing secreting glands whose fluids create an acidic pH in the range of about 4-5. In its normal state, the lining of the vagina secretes a fluid that is fermented to an acid by bacteria that are normally present. Many women harbor the yeast *Candida albicans* in the vagina and the peripheral areas around the vaginal opening and labia but most have no symptoms and it is harmless to them. This acidity of the vagina is a protective mechanism that helps to protect the vagina from invasion by other microorganisms.

Certain drug therapies can alter the balance of natural microorganisms that are present in the vagina, and hereby promote the growth of *Candida albicans*. Examples include the extended use of antibiotics, steroids and oral contraceptives with high estrogen content. Other factors that may cause *Candida* vaginitis include diabetes, pregnancy, using antihistamines, iron, folate, vitamin B12, or zinc deficiency. Tight fitting pants and the reactions to chemical ingredients found in soaps and detergents may also lead to *Candida* vaginitis.

Treatment with topical antifungal compositions, such as creams or suppositories, is normally the first choice of treatment for mild to moderate yeast infections. Serious infections, however, require a longer course of treatment. Formulation components which are released during the treatment process leak from the vagina creating unsanitary conditions and discomfort and also, more importantly, results in delivery of an unpredictable amount of the drug.

Another but not so frequent way of treating vaginal fungal infections is by using disposable articles such as tampons in order to decrease the pH. There are a number of common forms of disposable articles that are designed to absorb menstrual fluids discharged from a female's cervix, vaginal tampons, panty liners and sanitary napkins.

A wide variety of absorbent vaginal tampons has long been known in the art. Most currently commercially available tampons are made from a pledget of absorbent material comprising hydrophilic fibers such as cotton or viscose, which has been compressed into a substantially cylindrical form. Pledgets of a variety of types and constructions have been described in the art. Prior to compression, the pledget may be rolled, spirally wound, folded, or assembled as a rectangular pad of absorbent material. Tampons made from a generally rectangular pledget of absorbent material have been popular and successful in the market, for example, the tampon described in U.S. Pat. No. 4,294,253. As fluid is absorbed, these compressed tampons are expected to re-expand toward their original pre-compressed size, and to eventually become large enough to effectively cover the vaginal cavity against fluid leakage or bypass To avoid the discomfort of inserting the tampon into the vagina due to the "dry feel", a liquid pervious non-woven fabric cover layer is used to inhibit the shedding of fibers from the absorbent core. This is known from the disclosure of e.g. U.S. Pat. No. 4,816,100 and GB 2,010,680. This is due to the smoother nature of the non-woven fabric. Similar advantages can be obtained using plastics as cover layer material over the absorbent core of a tampon, as described in U.S. Pat. No. 5,374,258. Another method to render the tampon more comfortable is using friction-reducing agents for example: pectin hyaluronic acids, glycerides, waxes such as silicone waxes, plant waxes or paraffin as described in U.S. Patent application 2006/074391A1.

Tampons used for the treatment of fungal infections are already described in the art. U.S. Pat. No. 6,416,779, for example, describes tampons utilized for the treatment of fungal infections by intravaginal administration of therapeutic antifungal drugs to the vagina. Unlike the invention herein the tampon is just a delivery form for drugs and not a method of binding the fungi.

Another way of using sanitary articles for the treatment of fungal infections is by impregnating the tampons with pH-decreasing compounds as described in U.S. Patent application 2006/0264857 and U.S. Pat. No. 6,964,949. Further the WO application 1992/013577 discloses a tampon or sanitary napkin that is impregnated with a culture of living lactic acid producing bacteria, with the object of alleviating vaginal or urinary tract infections. The mechanism behind the antagonistic effect is not completely known but the dominating comprehension is that *Lactobacillus* having antagonistic properties have an ability of coaggregate with the pathogens, to produce inhibitors and to lower pH in the urogenital environment by the lactic acid production. Lactic acid bacteria require special protection during storage and therefore a more stable solution to the problem is preferable.

None of the above inventions and patents, taken either singularly or in combination, is seen to describe the instant invention, i.e. a way of combating vaginal fungal inventions utilizing the SORBACT® principle.

A typical sanitary napkin or panty liner includes a liquid pervious topsheet, a liquid impervious backsheet joined to the topsheet, and an absorbent core positioned between the topsheet and the backsheet. Nonwoven webs are often used as the topsheet because they are liquid pervious and provide a skin friendly surface. The absorbing material of the core normally comprises a hydrophilic material such as fibers. Suitable fibers include conventional hydrophilic cellulosic fibers, cotton fibers, viscose fibers or synthetic fibers, for example, polyester, polypropene or combinations thereof, and then pressed to a core.

WO2007073246 discloses an absorbent article for female use, such as a sanitary napkin preventing or reducing migration of microorganisms from the anus area to the urogenital area. This is achieved by a microorganism-hindering element or section, for preventing or reducing migration of microorganisms from the anus area to the urogenital area in the direction from the rear edge to the front edge of the article. The element or section comprises a material selected from one or more of a hydrophobic material, an antimicrobial agent and a positively charged material. The hydrophobic material can be selected from fatty acid esters but not as in the invention herein, which is from the fatty acid esters DACC and AKD, highly hydrophobic and specific for SORBACT® products. Also the microorganism-hindering section is just a limited part of the napkin in contrast to the invention herein where the whole topsheet is made of the SORBACT® material.

There are several known inventions relating to the use of antimicrobial substances and materials. One such example is found in U.S. Pat. No. 5,700,742, which relates to a method of treating a textile material to inhibit microbial growth and which comprises applying to the textile material an oligo or polymeric biguanide or salt thereof with an inorganic acid or an organic acid having a pK value above 4.5 followed by a strong organic acid having a pK value below 4.5 and free from any aliphatic or oxyalkylene chain containing 12 or more carbon atoms. A textile material treated in accordance with the claimed method is also disclosed.

U.S. Pat. No. 5,856,248 relates to cellulose fibers and products comprising cellulose fibers treated to absorb body secretions while substantially decreasing microbial growth, the fibers being chemically modified in a two-stage process comprising a first stage treatment with a water soluble salt of a transition metal and an alkali and a second stage treatment with a solution of a bisbiguanide compound, thereby forming a bond between the cellulose fibers, the transition metal and the compound. The process may utilize a rinsing step to neutral pH between the two aforementioned stages.

U.S. Pat. No. 5,817,325 relates to an article of manufacture having disposed on a surface thereof a non-leaching antimicrobial coating which kills microorganisms upon contact. The coating comprises an organic polycationic polymer matrix immobilized on the surface having bound or complexed thereto a surface-accessible antimicrobial metallic material such that the antimicrobial material does not release biocidal amounts of elutables into the surrounding environment.

Further, U.S. Pat. No. 6,160,196 relates to the same principle but adds thereto an antimicrobial active compound which is adapted to prevent infections from the outside of the pad and the antimicrobial compound is not released into the wound. U.S. Pat. No. 4,211,227 discloses a non-woven surgical sponge material comprising a layered fabric having an inner core or a substantially hydrophilic material disposed adjacent at least one outer or surface layer, or between a pair of outer layers, of a substantially hydrophobic material. The sponge material is bonded by passing the material through rolls engraved in a pattern of lands and grooves such that a repeating pattern of three degrees of compression are imposed on the material. However, the so-produced sponge does not use a hydrophobic material binding microorganisms to any great extent.

U.S. Patent Application 2006/0163149 relates to a product for absorption, whereby a hydrophobic entity and a positively charged entity are connected to a support matrix. In this method, the hydrophobic entity may be connected by using DACC, and the positively charged entity may be connected by using polyethyleneimine. Preferred fields of the application are filters, face masks, wound dressings, nasal sprays, and drapes for use during surgical intervention etc. However sanitary protection articles are not mentioned in this application nor are the treatment against fungal vaginal infections.

Even if traditional sanitary protection products solve an important problem absorbing blood, they do not have an antifungal property without additional compounds like drugs, lactic acid bacteria and pH decreasing compounds.

It is therefore a primary object of this invention to provide a device, composition and a method for prevention of fungal vaginal infections especially those caused by *Candida albicans* by providing an intravaginal tampon or a sanitary napkin/panty liner comprising a conventional absorbent covered with a cover layer treated according to the SORBACT® principle.

SUMMARY OF THE INVENTION

A primary object of the present invention is to provide disposable, absorbent articles such as tampons, sanitary napkins and panty liners for the treatment of vaginal fungal infections especially caused by *Candida albicans*. An object of the present invention is to use a hydrophobic and/or cation active material as a cover layer, attached to a conventional absorbent layer, for the binding of the fungi. Another object is to render the cover layer hydrophobic due to the SORBACT® principle i.e. treating the fabric with DACC and/or AKD and/or making the fabric cationic.

Other objects and advantages of the present invention will become obvious to the reader and it is intended that these objects and advantages are within the scope of the present invention.

DETAILED DESCRIPTION OF THE INVENTION AND PREFERRED EMBODIMENTS THEREOF

The invention herein relates to absorbent sanitary protection products. The invention is a SORBACT® material combined with the absorbent part of a device comparable to a common catamenial sanitary product such as tampons, sanitary napkins and panty liners. The invention is able to absorb blood and fluids and at the same time, selectively bind and remove unwanted fungi. The fungi are preferably *Candida albicans* but could be any fungi causing vaginal infections, for example, *Candida crusei* and *Candida parapsilosis*. The fungi bind to the SORBACT® material within 30 seconds. The test in Example 1 shows that the device is a good adsorber of different important and potential pathogens.

Sanitary Napkins and Panty Liners

Figure 1:
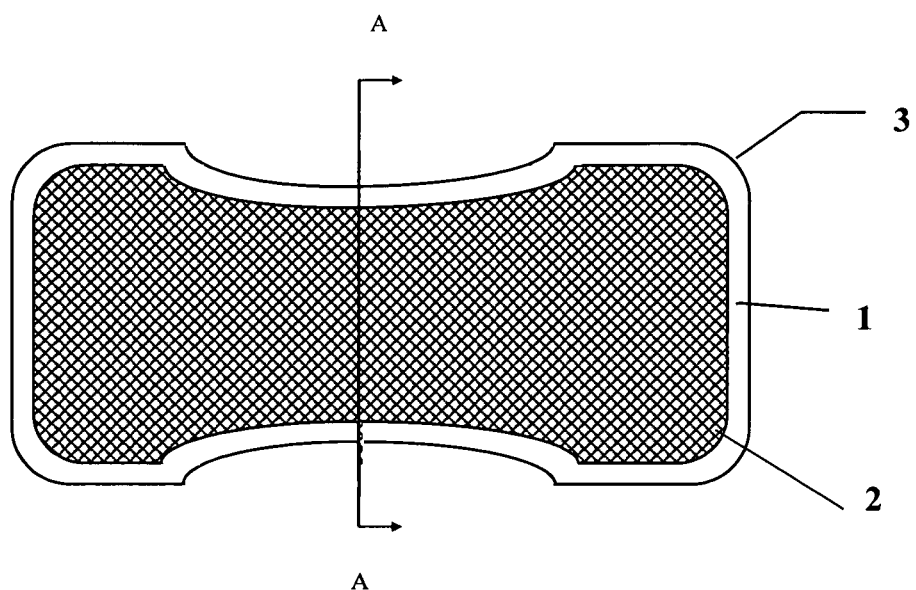
FIG. 1 is a plan view of a device, which can be a sanitary napkin or panty liner.
Figure 2:
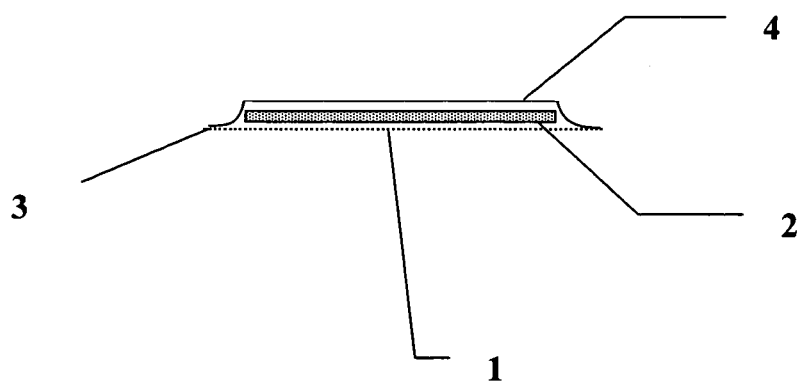
FIG. 2 is a cross-sectional view of the catamenial device of FIG. 1.

With respect to the drawings, FIG. 1 is a perspective view of a device, which may be a sanitary napkin or panty liner or the like, showing the topsheet (1) with SORBACT® properties. The absorbent core (2) is seen through the topsheet (1). The edge (3) is where the topsheet (1) is joined to the backsheet (4) (not shown in this figure). FIG. 2 is a cross-sectional view of a device, that can be a sanitary napkin or panty liner or other absorbent device, having a body-contacting topsheet (1), having SORBACT® properties. The topsheet (1) is joined to the backsheet (4), and a core (2), disposed between the topsheet (1) and backsheet (4). The topsheet (1), the backsheet (4) and the absorbent core (2) may be assembled in a variety of well known configurations, exemplary containment assembly configurations are described generally in U.S. Pat. No. 3,860,003

The absorbent core (2) may be any absorbent member which is generally compressible, conformable, non-irritating to the wearer's skin, and capable of absorbing and retaining liquids. The absorbent core (2) may be manufactured in a wide variety of sizes and shapes for example, rectangular, hourglass, "T"-shaped, asymmetric, etc, and from a wide variety of liquid-absorbent materials commonly used in disposable absorbent articles. The absorbing material of the core used in the invention will normally comprise a hydrophilic material such as fibers. Suitable fibers include conventional hydrophilic cellulosic fibers, cotton fibers, viscose fibers, cellulose acetate or synthetic fibers, for example polyester, polypropene or combinations thereof, which are then pressed to form a core. The absorbent core can contain superabsorbents, for example, sodium acrylate-acrylic-acid polymers or crosslinked dimethyl cellulose.

The backsheet (4) is preferably impervious to liquids and is preferably manufactured from a thin plastic film, although other flexible liquid impervious materials known in the art may also be used. Preferably the backsheet (4) comprises a polymeric film such as thermoplastic films of polyethylene or polypropylene. The basic weight of the backsheet (4) can range between 12-40 g/m². The topsheet (1) is positioned adjacent the body-facing surface of the absorbent core (3) and is preferably joined thereto and to the backsheet (4) making an edge (3), by attachment means (not shown) such as those well known in the art.

The backsheet can also be made of liquid impervious but breathable nonwoven or breathable plastic film.

The topsheet (1) is preferably compliant, soft feeling, and non-irritating to the wearer's skin. Further, the topsheet (1) is liquid pervious permitting liquids to readily penetrate through its thickness. A suitable topsheet (1) is manufactured from a nonwoven or textile web of synthetic fibers (e.g., polyester, polyethylene, or polypropylene fibers or bicomponent fibers). Other suitable fibers include natural fibers such as wood, cotton, or rayon, or combinations of natural and synthetic fibers.

The topsheet (1) is rendered hydrophobic by the treatment with DACC and/or AKD in order to bind the fungi, according to the SORBACT® principle described in U.S. Pat. No. 4,617,326 and U.S. Patent Application 2006/0129080. The topsheet (1) is rendered cation active, by means described in U.S. Pat. No. 4,617,326 and U.S. Patent application 2006/0129080 or the by application of cationic dyes known in the art. The basis weight of the topsheet (1) can range between 10-100 g/m². The backsheet (4) is joined to the absorbent core (3) by attachment means such as those well known in the art. For example, the backsheet (4) may be secured to the absorbent core (3) by a uniform continuous layer of adhesive, a patterned layer of adhesive, or an array of separate lines, spirals, or spots of adhesive. The adhesive could be any well known in the art.

Figure 6:
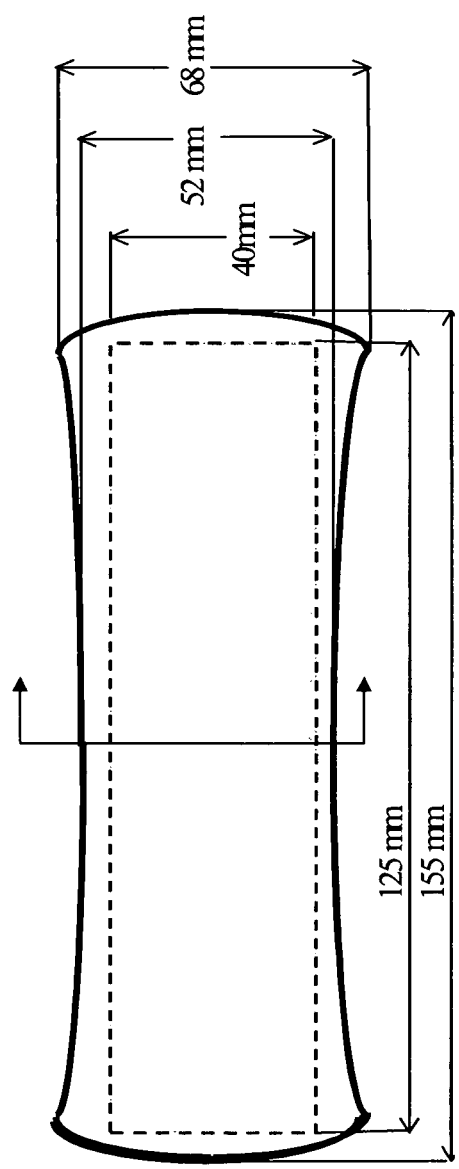
FIG. 6 is a top plan view of a catamenial device of FIG. 1, including dimensions.

The dimensions of a panty liner of the invention herein are described in, but not limited to FIG. 6. The length of the panty liner is preferably 155 mm. The length of its absorbent layer is preferably 125 mm and the width is preferably 40 mm. The panty liner is preferably 52 mm at its narrowest spot (in the middle) and 68 mm in its widest spots (at the ends).

The sanitary napkin or panty liner may also be provided with additional features commonly found in sanitary napkins, including "wings" or "flaps" (not shown) as is known in the art, and/or a fluid acquisition layer between the topsheet (1) and the core (2). The topsheet (1) of the device of the present invention may also have lotion composition disposed onto at least the body-contacting surface.

Tampons

Figure 3:
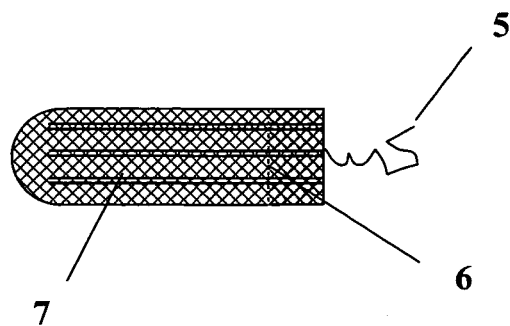
FIG. 3 is an elevational view of a tampon.

With respect to the drawings, FIG. 3 shows a tampon having a generally cylindrical shape. Surrounding the absorbent core is a liquid pervious cover of the hydrophobic and/or cationactive SORBACT® material (6). A cord (5) is secured to the end portion for easy removal of the tampon. The introduction end of the tampon is designed as a constriction resembling a round dome. As a result of the pressure applied, the tampon is provided with press notches (grooves) (7) arranged distributed over equal circumferential angles.

Figure 4:
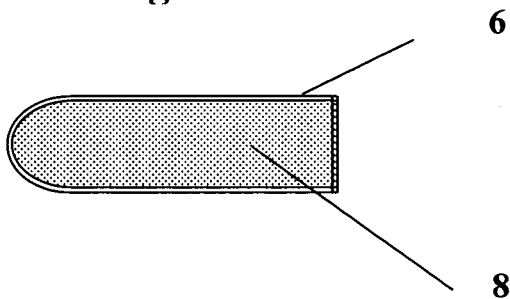
FIG. 4 is a lengthwise cross-sectional view of the tampon of FIG. 3.

FIG. 4 is a cross-sectional view of a tampon in its longitudinal direction, having an absorbent core (8) of generally cylindrical shape. Surrounding the absorbent core (8) is a liquid pervious cover layer of hydrophobic and/or cationactive SORBACT® material (6).

Figure 5:
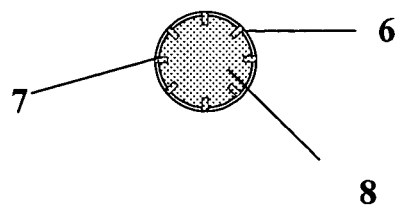
FIG. 5 is a cross-sectional view of the tampon of FIG. 3, perpendicular to the lengthwise axis of the tampon.

FIG. 5 is a cross-sectional view of a tampon perpendicular to its linear axis. Surrounding the absorbent core (8) is a liquid pervious cover layer of hydrophobic and/or cationactive SORBACT® material (6). The tampon is pressed radially to give the final form. As a result of the pressure applied, the tampon is provided with press notches (grooves) (7) arranged distributed over equal circumferential angles as shown in FIG. 5.

The tampon can be packaged in a conventional cover wrap for use as a digital tampon or within an applicator package for insertion by means of an applicator. The tampon within the wrapper can favorably be sterile. Suitable methods of sterilizing include gamma and electron beam irradiation methods.

As used herein, the term "woven web" refers to a web that has a structure of individual fibers or threads which are joined together in a regular, repeating manner. While the fibers in the "nonwoven web" are not joined together in any regular, repeating manner.

With respect to the above description then, it is to be realized that the optimum dimensional relationships for the parts of the invention, to include variations in size, materials, shape, form, function and manner of operation, assembly and use, are deemed readily apparent and obvious to one skilled in the art. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The features of the present invention will be more clearly understood by reference to the following examples, which are not to be construed as limiting the invention.

Example 1

Working Example Tampons

The tampon in FIGS. 3, 4 and 5 has a length of 50 mm and diameter of 12.5 mm and a total weight of 2.5 g with an absorbent core (8) made of 100% viscose fibers (Lenzing GmbH, Germany). The tampon is surrounded with a cover layer (6) composed of a thermo bonded nonwoven made of polyethylene/polyester with a surface weight of 12 g/m² (Far eastern Textile, Taiwan), this nonwoven is made hydrophobic with DACC (Di Alkyle Carbamoyle Cloride) and made cationic by coloring with cationic dyes (Terasil yellow 4G and Teratop blue BGE, CIBA GmbH). The tampon is provided with 120 mm long cotton cord (5), for easy removal of the tampon after use. The cover layer is bonded to the absorbent core by compression. The tampon is compressed to its outer diameter with 8 groves (7). The final product is covered with cellophane film with a surface weight of 20 g/m², to be removed before use.

Example 2

Working Example Panty Liners

Figure 7:
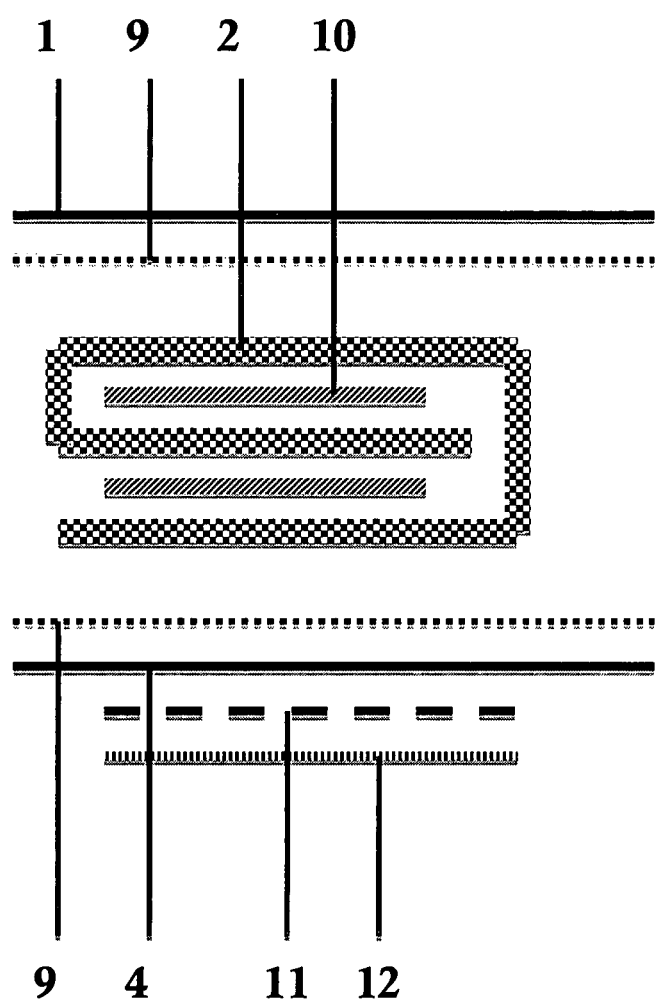
FIG. 7 is a detailed cross-sectional view of a catamenial device, along the arrows in FIG. 6

Panty liner with dimensions according to FIGS. 6 and 7, show the top sheet (1) which is in direct contact with the body, made of a nonwoven Viscose/Polyester fiber with a surface weight of 40 g/m² (Aquadim VE 40, from Tharreau Industries, France). This nonwoven is made hydrophobic with DACC (Di Alkyle Carbamoyle Cloride and made cationic by the coloring with cationic dyes (Terasil yellow 4G and Teratop blue BGE, CIBA GmbH). The topsheet (1) is fastened to an absorbent core (2), with an adhesive (9), (Fuller D8370ZP, Fuller GmbH, Germany). The absorbent core (2) is made of Air laid cellulose, (Concert GmbH, Germany) having a surface weight of 60 g/m² having an unfolded width of 155 mm. The absorbent core (2) is folded in to three layers to a final width of 40 mm. The length of the absorbent layer is 125 mm.

Between the absorbent layers there is 0.3 g of superabsorbent (10) (FIG. 7) (SX Fam, Stockhausen, GmbH) evenly spread or mixed along the whole length of the absorbent layer. The absorbent layer is fastened, to a backsheet (4) that functions as a moisture barrier, with the same type of adhesive (9) as the top layer (Fuller D8370ZP, Fuller GmbH, Germany). The Backsheet (4) (moisture barrier) is made of polyethylene film with a thickness of 0.02 mm, (Trioplast AB, Sweden). The outside of the panty liner does have a self sticking adhesive (11) (Fuller 3964, Fuller GmbH, Germany) located on the outside of the moisture barrier.

The sticking layer (11) is protected with a Siliconized paper (12) (RP40 Rosella RSL, Italy), which is to be removed before use.

Example 3

In Vitro Test of the Tampons and Sanitary Napkins/Panty Liners to Bind Pathogens Material: The absorbent products as described in Example 1 and 2

Bacterial strains: *Staphylococcus aureus* Newman, *Pseudomonas aeruginosa* 510, *Enterococcus faecalis*, *Candida albicans*

Isolates were cultured on agar with 5% horse erythrocytes in 5% $CO_2$ atmosphere at 37° C. Suspensions were made in phosphate-buffered saline (PBS, 0.02 M sodium phosphate and 0.15 M sodium chloride, pH 7.2) at $10^9$ bacterial cells/ml, $10^7$ fungal cells/ml or indicated concentration.

The products were cut in 1 cm² pieces. Incubation was made in 24 well polymer plates. 1 ml of suspension was added to each piece. The plates were placed on a rotary shaker at very low speed. Incubation was performed at room temperature for the indicated time. After incubation, dressings were rinsed in PBS several times, and then put in 2.5% TCA (tricarboxylic acid).

The ATP content was measured in a luminometer (LKB Wallac). Controls: Number of adhered bacteria (CFU/ATP) were normalized against total added bacteria (CFU/ATP), and blank (no bacteria, only EDTA-Tris buffer) was the ATP value control.

Results:

*S. aureus* >$10^5$ cells adhered during 30 sec, 1, 5 and 10 minutes, and then increased to $10^6$ cells after 2 hrs. Some multiplication occurred during the following 24 hrs to reach $5 \times 10^6$ cells/cm².

*P. aeruginosa* Around $10^6$ cells adhered during 30 s, 1, 5 and 10 min, and then increased during 30 and 60 min incubation to reach $10^7$ cells/cm² after 2 hrs incubation. No multiplication of adhered bacteria occurred during the following 24 hrs.

We did not reach endpoints for maximal adsorption. When $5 \times 10^9$ cells of *S aureus* were added, $10^8$ cells adhered, for *P. aeruginosa* $10^8$ cells adhered out of $10^{9.5}$ added, and for *E. faecalis* $8 \times 10^6$ out of $5 \times 10^{10}$ added. For *C. albicans* the slope levels off, $10^5$ cells adhered out of 5 added.

The results did not differ between the tampons and the sanitary napkins/panty liners.

Example 4

In Vivo Test of the Tampon for the Treatment of Vaginal *Candida albicans* Infections In order to test the effect of the tampons of the invention herein a pilot study was performed. Eight patients participated in the study, and seven of them were given treatment. The patients were women between the ages of 19-45. The anamnesis of six of the eight patients was infrequent fungallike vaginal infections. For one of the patients the anamnesis was frequent fungal vaginal infection after coitus with the same partner.

Seven of the patients were treated with tampons of the invention herein twice a day for five days. They were prescribed to use the first tampon before bedtime and the second the following day, for four hours. Two of the patients suffered from itching and burning both in the vulva and the vagina, symptoms characteristic of fungal vaginal infections. However they lacked the typical whitish discharge. The treatment with the tampon of the invention herein did not affect the symptoms of these two women. At the next appointment one of the two patients was tested negative for *Candida albicans* (the other patient was not tested at all). The patient suffering from itching and burning after coitus was recommended to insert a tampon after coitus and keeping it overnight. She successfully tested it four times. None of the previous symptoms remained. Four of the remaining five patients became free of symptoms after the recommended treatment. The symptoms of the last of the remaining five patients were clearly improved. With additional per oral fungal treatment the patient became free of symptoms. No side effects were registered.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method for binding and removing fungi associated with vaginal fungal infections, comprising: providing a device for treatment of a patient with a vaginal fungal infection, comprising: a) a core of absorbent material having a shape selected from the group consisting of a flat shape and a cylindrical shape; and b) a liquid pervious layer covering the core and forming a topsheet which is in direct contact with a user of the device, wherein the topsheet is treated to adsorb fungal yeast, and treating the patient having the vaginal fungal infection with the device, wherein treating the patient consists of contacting the patient with the topsheet which causes fungal yeast cells to be bound to the topsheet and removed from the patient, and wherein the device has no antifungal property provided by additional compounds including drugs, lactic acid bacteria or pH decreasing compounds.

2. The method of claim 1, further comprising providing superabsorbents within or applied to the core.

3. The method of claim 1 further comprising making the absorbent core of fibers selected from the group consisting of a) natural fibers selected from the group consisting of cellulose, viscose cellulose acetate and cotton fibers; and b) synthetic fibers selected from the group consisting of polypropylene, polyester and polypropylene-polyester fibers.

4. The method of claim 3, further comprising providing superabsorbents within or applied to the core.

5. The method of claim 1 further comprising treating the topsheet with a substance selected from the group consisting of dialkyl carbamoyl chloride and alkyl ketene dimer.

6. The method of claim 1 further comprising positively charging the topsheet.

7. The method of claim 1 further comprising treating the topsheet with fatty acid esters so that the top layer has a strong hydrophobic property.

8. The method of claim 7 further comprising treating the topsheet with a substance selected from the group consisting of dialkyl carbamoyl chloride and alkyl ketene dimer.

9. The method of claim 1 further comprising making the topsheet from a material selected from the group consisting of a) a nonwoven or textile web of synthetic fibers; b) natural fibers; and c) combinations of natural and synthetic fibers.

10. The method of claim 9 further comprising making the topsheet from a material selected from the group consisting of polyester, polyethylene, polypropylene and bicomponent fibers.

11. The device of claim 9 wherein the topsheet is make from a material selected from the group consisting of wood, cotton, rayon, and cellulose acetate.

12. The method of claim 1, wherein the core has a flat shape, and wherein the device further comprises an impervious backsheet on the opposite side of the core as the topsheet.

13. A method for binding and removing fungi associated with vaginal fungal infections, comprising: providing a device for treatment of a patient with a vaginal fungal infection, comprising: a) a core of absorbent material having a shape selected from the group consisting of a flat shape and a cylindrical shape, and made of fibers selected from the group consisting of a) natural fibers selected from the group consisting of cellulose, viscose cellulose acetate and cotton fibers; and b) synthetic fibers selected from the group consisting of polypropylene, polyester and polypropylene-polyester fibers; and b) a liquid pervious layer covering the core and forming a topsheet which is in direct contact with a user of the device, wherein the topsheet is treated to adsorb fungal yeast with a substance selected from the group consisting of dialkyl carbamoyl chloride and alkyl ketene dimer, and treating the patient having the vaginal fungal infection with the device, wherein treating the patient consists of contacting the patient with the topsheet which causes fungal yeast cells to be bound to the topsheet and removed from the patient wherein the device has no antifungal property provided by additional compounds including drugs, lactic acid bacteria or pH decreasing compounds.

14. The method of claim 13, further comprising providing superabsorbents within or applied to the core.

15. The method of claim 13 further comprising positively charging the topsheet.

16. The method of claim 13 further comprising making the topsheet from a material selected from the group consisting of polyester, polyethylene, polypropylene and bicomponent fibers.

17. The device of claim 13 wherein the topsheet is make from a material selected from the group consisting of wood, cotton, rayon, and cellulose acetate.

18. The method of claim 13, further comprising providing that the core has a flat shape, and providing an impervious backsheet on the opposite side of the core as the topsheet.

19. The method of claim 18, further comprising making the core of three layers of material.

20. The method of claim 13, wherein the device is selected from the group consisting of intravaginal tampons, sanitary napkins, and panty liners.

21. The method of claim 13, wherein the fungal vaginal infections are infections of *Candida albicans*.

* * * * *